(12) United States Patent
Blakley

(10) Patent No.: US 7,135,806 B2
(45) Date of Patent: Nov. 14, 2006

(54) TRANSDUCER-BASED SENSOR SYSTEM WITH MULTIPLE DRIVE SIGNAL VARIANTS

(75) Inventor: Daniel Robert Blakley, Philomath, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 753 days.

(21) Appl. No.: 10/286,071

(22) Filed: Oct. 31, 2002

(65) Prior Publication Data

US 2005/0258716 A1    Nov. 24, 2005

(51) Int. Cl.
*H01L 41/08* (2006.01)

(52) U.S. Cl. ............... 310/316.01; 310/317; 310/319; 310/321; 310/334; 600/447; 73/626

(58) Field of Classification Search ........... 310/316.01, 310/317, 319, 334; 73/626; 600/447
See application file for complete search history.

(56) References Cited

U.S. PATENT DOCUMENTS

| | | | |
|---|---|---|---|
| 3,582,838 A | 6/1971 | DeVries | |
| 3,983,424 A | 9/1976 | Parks | |
| 4,055,072 A | 10/1977 | Fletcher et al. | |
| 4,224,829 A | 9/1980 | Kawabuchi et al. | |
| 4,241,610 A | 12/1980 | Anderson | |
| 4,788,466 A | 11/1988 | Paul et al. | |
| 5,172,343 A * | 12/1992 | O'Donnell | 367/7 |
| 5,201,215 A | 4/1993 | Granstaff et al. | |
| 5,269,307 A | 12/1993 | Fife et al. | |
| 5,448,126 A | 9/1995 | Eda et al. | |
| 5,477,098 A | 12/1995 | Eguchi et al. | |
| 5,706,818 A * | 1/1998 | Gondo | 600/447 |
| 5,817,023 A * | 10/1998 | William Daft | 600/447 |
| 5,827,188 A * | 10/1998 | Wright et al. | 600/447 |
| 6,144,332 A | 11/2000 | Reindl et al. | |
| 6,679,846 B1 * | 1/2004 | Napolitano et al. | 600/447 |
| 6,679,847 B1 * | 1/2004 | Robinson et al. | 600/447 |
| 2002/0011761 A1 | 1/2002 | Takeuchi et al. | |

FOREIGN PATENT DOCUMENTS

| | | |
|---|---|---|
| GB | 941573 | 11/1963 |
| JP | 54-155683 | 12/1979 |
| JP | 55-40967 | 3/1980 |
| JP | 7-506736 | 7/1995 |
| WO | WO 01/02857 | 1/2001 |

OTHER PUBLICATIONS

"In Situ Interfacial Mass Detection With Piezoelectric Transducers", Michael D. Ward et al., Science, vol. 249, Issue 4972, Aug. 31, 1990, pp. 1000-1007.

"A Novel Immunosensor for Herpes Viruses", Bernd Konig et al., Analytical Chemistry, vol. 66, No. 3, Feb. 1, 1994, pp. 341-344.

(Continued)

*Primary Examiner*—Mark Budd

(57) ABSTRACT

A sensor system including a plurality of transducer groups, with each transducer group having a plurality of transducers. The transducers of each group are adapted to be placed in operative proximity with a sample material. Within each transducer group, each transducer is actuable via application of a different phase-shifted variant of a local oscillator signal to the transducer. The sensor system is also configured so that, for each transducer group, the phase-shifted variants of the local oscillator signal are selectively employed during output processing to inhibit cross-transducer interference occurring between simultaneously active transducers.

39 Claims, 2 Drawing Sheets

OTHER PUBLICATIONS

"Piezoelectric Mass-Sensing Devices as Biosensors—An Alternative to Optical Biosensors?", Andreas Janshoff et al., The Quarz-Crystal Microbalance in Life Science, Amer. Chem. Int. Ed. 2000, 39, pp. 4004-4032.

"'Hearing' Bond Breakage, Measurement of Bond Rupture Forces Using a Quartz Crystal Microbalance", F. N. Dultsev et al., Langmuir 2000, 16, pp. 5036-5040.

"Listening for Viral Infection", Erica Ollmann Saphire et al., Nature Biotechnology, Sep. 2001, vol. 19, pp. 823-824.

"Direct and Sensitive Detection of a Human Virus by Rupture Event Scanning", Matthew A. Cooper et al., Nature Biotechnology, Sep. 2001, vol. 19, pp. 833-837.

\* cited by examiner

TRANSDUCER-BASED SENSOR SYSTEM WITH MULTIPLE DRIVE SIGNAL VARIANTS

BACKGROUND

Transducer devices are used in a variety of applications to transfer energy between electrical systems and mechanical systems. Quartz crystal microbalance (QCM), for example, is a transducer-based technology that may employ piezoelectric transducers in various configurations to perform sensing functions. QCM technology takes advantage of the fact that the resonant frequency of a transducer typically varies with the effective mass of the transducer. Accordingly, when portions of a sample material binds to the transducer, the mass of the bonded sample material can be detected by monitoring the resonant frequency of the vibrating mass, relative to a predetermined reference.

A related technology is rupture event scanning (RES), in which transducers may be employed to produce mechanical energy to break bonds within a sample material. In addition to providing energy to break the bonds, the transducers may be used as sensors to analyze acoustic events (e.g., a pressure wave) that can occur when bonds break. Different types of bonds have unique properties that produce distinctive acoustic events. The bonds can be identified and analyzed by using various techniques to study the acoustic events.

Transducer systems such as those described above typically employ multiple distinct transducers. The transducers are often provided in an array, with some type of mechanical suspension being used to suspend the transducers in place relative to a base or other stationary component of the system.

Although many prior systems have multiple transducers, typically only one transducer can be activated at any given time. Alternatively, where multiple transducers are simultaneously active, the activated transducers commonly must be separated by a relatively large physical distance. The reason for this is undesired signal coupling that can occur when physically proximate transducers are active at the same time.

One type of undesired coupling results from the liquid that is often used to hydrate biological samples in QCM and RES applications. Where a well of liquid is spread across multiple transducers, or even where separate liquid wells are employed for each transducer in a multiple-transducer configuration, mechanical vibration produced by one transducer can be transmitted through the liquid (and through intervening structures) to other transducers in the system. Accordingly, when the transducers are simultaneously activated, the electrical signal sensed at the second transducer will then include interference produced by the vibration of the first transducer. The mechanical suspension that holds the transducers in place can also transmit vibration from one transducer to another, even though such suspensions typically are designed to minimize this effect. Finally, stray capacitance and other indirect electrical coupling can produce interference when physically proximate transducers are activated simultaneously.

Because prior systems typically do not provide for simultaneous activation of physically proximate transducers, they may be limited in processing speed and may not be able to provide a satisfactory level of performance in applications where it is desirable to operate multiple transducers at the same time.

SUMMARY

A sensor system is provided according to one aspect of the invention. The sensor system includes a plurality of transducer groups, with each transducer group containing a plurality of transducers. The transducers of each group are adapted to be placed in operative proximity with a sample material. The sensor system is configured so that, within each transducer group, each transducer is configured to be actuated by receiving a different phase-shifted variant of a local oscillator signal. The sensor system is also configured so that, for each transducer group, the phase-shifted variants of the local oscillator signal are selectively employed during output processing to inhibit cross-transducer interference occurring between simultaneously active transducers.

DETAILED DESCRIPTION

Figure 1:
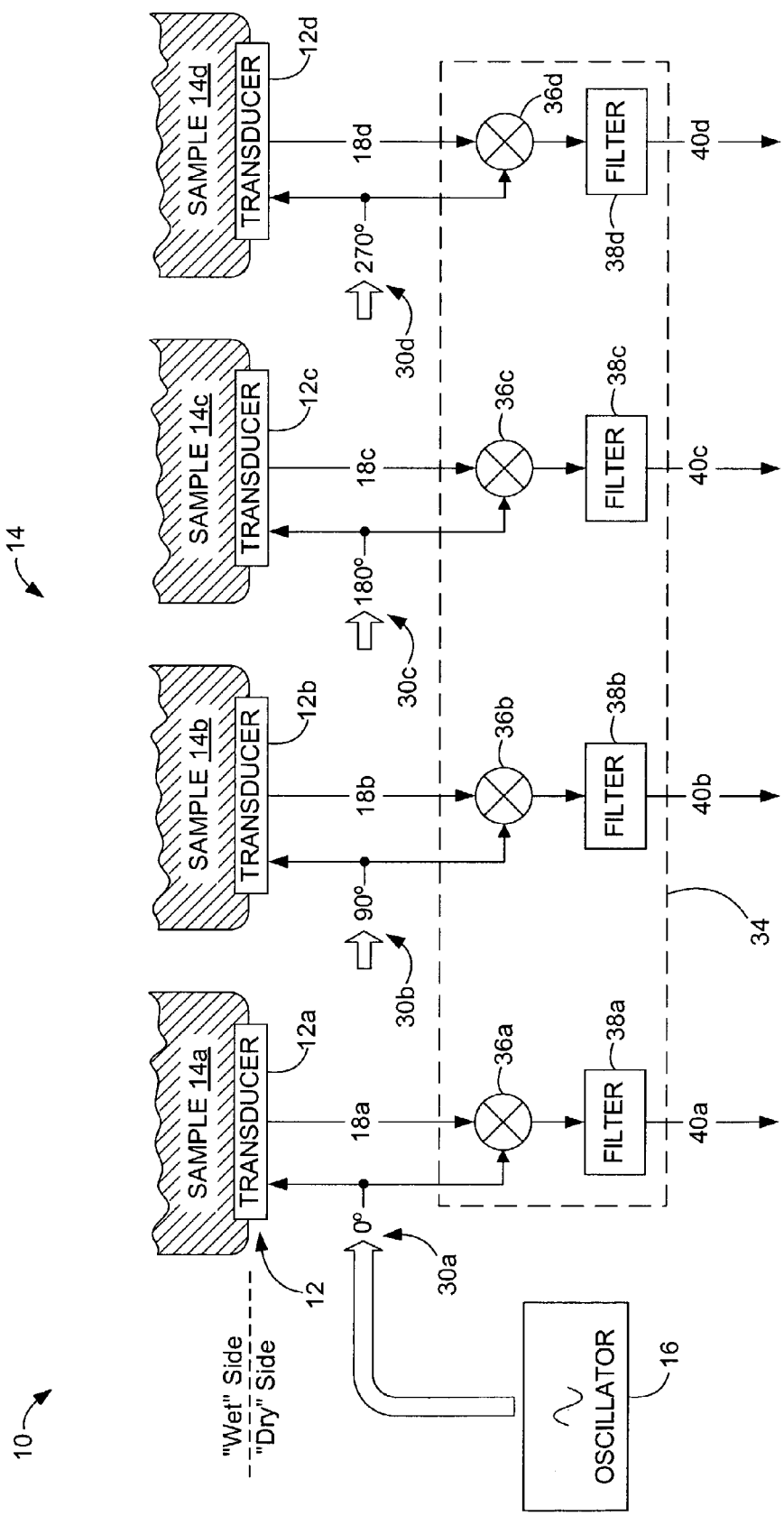
FIG. 1 is a schematic depiction of an embodiment of a transducer-based sensor system.

FIG. 1 depicts an exemplary sensor system 10, including a group 12 of transducers 12a, 12b, 12c and 12d. The transducers may be placed into contact with, or in close proximity to, a test material such as sample 14. The test material may be provided as one contiguous sample spread across multiple transducers, or may be provided as separate portions 14a, 14b, 14c and 14d in a well, receptacle or like container associated with each transducer, as in the depicted example. Typically, the transducers are coupled with a signal generator, such as oscillator subsystem 16, via which activating signals are applied to the transducers. The transducers typically are also coupled with additional electronic components adapted to facilitate sensing functions, as will be explained in detail below.

Figure 2:
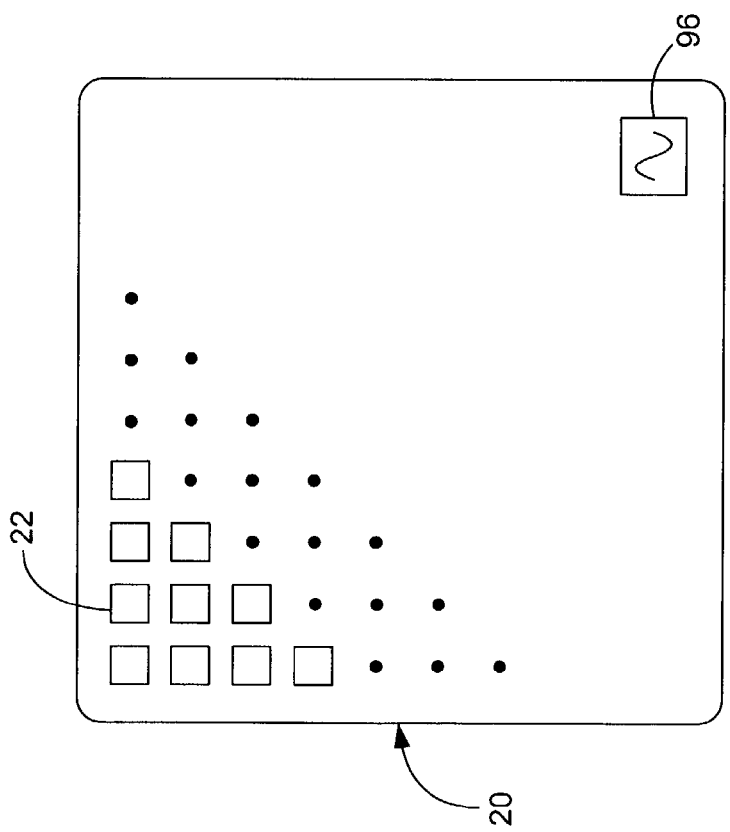
FIG. 2 is a schematic depiction of an embodiment of a transducer array, including a plurality of transducer groups, which may be configured similarly to the transducer group shown in FIG. 1.

The depicted transducers may take a variety of configurations, and may be implemented in different sizes and shapes, and with different materials, as desired and appropriate for a given application. In some embodiments, the transducers are implemented within a microchip as an array of piezoelectric crystals, or as an array of surface acoustic wave devices, surface-skimming bulk wave devices or Love-wave devices. FIG. 2 depicts such an exemplary array 20, including a plurality of groups 22 of transducers. As with the exemplary group shown in FIG. 1 (i.e., group 12), each of the groups shown in FIG. 2 may include four transducers. Alternatively, any other practicable number of transducers may be employed within the individual groupings. In single-chip embodiments, the supporting electronics typically are implemented at least partially on the chip along with the transducers.

Referring again to FIG. 1, the activating signals applied from oscillator subsystem 16 may cause the transducers to vibrate or undergo other movements. Typically, movement of the transducers is dependent not only on the characteristics of the activating signal, but also on the physical characteristics of the transducer and/or on physical phenomena occurring around the transducer. For example, the response of a transducer to a given activation signal will depend on the resonant frequency of the transducer. Resonant frequency, in turn, varies with the mass bound to the transducer. Accordingly, the character of a transducer's vibration may be affected by matter that bonds to the surface of the transducer to thereby vary the effective mass of the transducer. In addition, phenomena occurring within sample 14, or at the surface of the transducer, can affect transducer movement. For example, breaking of chemical bonds can produce a sonic event (also referred to as an acoustic event) that can contribute to the vibratory movement of a transducer.

In typical embodiments, vibrations and other movement may produce electrical output signals on output lines 18a, 18b, 18c and 18d. Analysis of these electrical signals can produce valuable information about sample 14. For example, such analysis can yield information about whether, and to what extent, portions of the sample have bonded to the surface of the transducers. Information may also be obtained about whether the sample contains certain types of matter, for example, by analyzing signals produced by rupture and other events.

In many applications, to achieve sufficiently accurate sensing, it will be desirable that the signal on any given transducer output line (e.g., lines 18a, 18b, 18c or 18d) correspond only to physical and electrical occurrences associated with the particular transducer, or with phenomena occurring within sample 14 in the immediate vicinity of that transducer. In practice, however, simultaneous operation of more than one transducer can result in cross-transducer noise components on individual transducer output lines. For example, in a non-ideal noisy system, the electrical signal on output line 18a may have components resulting from the movement of transducers 12b, 12c or 12d. Because these signal components typically are undesired and correspond to transducers other than transducer 12a, they may be referred to as cross-transducer noise, or cross-transducer noise components.

In many embodiments, the transducers (e.g., transducers 12a, 12b, 12c and 12d) are suspended relative to a base or other stationary structure (not shown) with a mechanical suspension (not shown). Typically, the mechanical suspension is connected to all of the transducers but is designed to allow each transducer to move independently. Moreover, the suspension structure is specifically designed to maximize this independence and thereby minimize crosstalk, or cross-transducer coupling. Although the transducers are substantially independent of one another, there often is some undesired cross-transducer coupling of vibrations and/or other movements through the suspension structure. Vibration of transducer 12a, for example, may couple through the mechanical suspension to produce a vibration in transducer 12b. This would contribute a cross-transducer noise component to the electrical signal on output line 18b.

Typically, the various circuitry coupled with the transducers is at least partially isolated to facilitate obtaining noise-free output signals for each individual transducer. In practice, however, there is often undesired electrical coupling between the circuitry of simultaneously active transducers. This may occur, for example, as a result of stray capacitance, stray mutual inductance, and/or other indirect electrical coupling. Stray capacitance between output lines 18a and 18b, for example, could introduce undesired noise components into the signals on those lines.

In many cases, it will be desirable to employ a liquid within or around sample 14. In biological scanning systems, for example, liquid may be employed to hydrate various types of sample materials. Typically, the liquid is provided within or around each portion of the sample material on one side of the transducer array, such that the transducer array has a "wet side" and a "dry side," as indicated in the example of FIG. 1. Use of such a liquid environment can be another source of cross-transducer noise, as discussed above.

As shown in FIG. 1, oscillator subsystem 16 may be configured to apply different variants of an oscillator signal to the other components of sensor system 10. Typically, the base signal is a sinusoid, and the subsystem generates a number of phase-shifted variants of this signal for use within sensor system 10. As explained in more detail below, the phase-shifted variants may be applied as inputs to produce vibrations or other movement in the transducers. In addition, as also explained below, the phase-shifted variants may be employed during processing of output signals produced by the transducers.

In the depicted embodiment, oscillator subsystem 16 is configured to output four different variants of a sinusoidal local oscillator (LO) signal: (1) a first variant 30a that is in phase with the LO, or 0°, (2) a second variant 30b that is shifted in phase from the LO by 90°, (3) a third variant 30c that is shifted in phase from the LO by 180° and (4) a fourth variant 30d that is shifted in phase from the LO by 270°. These phase-shifted variants typically are all the same frequency as the local oscillator, and may be respectively referred to as the 0° variant, 90° variant, 180° variant and 270° variant.

As shown in FIG. 1, each of the different phase-shifted variants may be applied as an input to a corresponding one of the transducers. In the depicted example, the 0° variant is applied to transducer 12a, the 90° variant is applied to transducer 12b, and so on. As explained below, application of different phase-shifted variants to the transducers may allow an output processing subsystem 34 to isolate and extract output signals from the individual transducers, free from the cross-transducer interference described above.

In order to suppress cross-transducer interference, it will be desirable in many cases to employ the same phase-shifted variants during processing of output signals produced by the transducers. Indeed, exemplary output processing subsystem 34 may be configured to employ the phase-shifted variants to isolate and extract output signals from the transducers.

As in the depicted example, output processing subsystem 34 may include, for each of transducers 12a, 12b, 12c and 12d, a corresponding mixer section (36a, 36b, 36c and 36d, respectively) and a low pass filter (38a, 38b, 38c and 38d, respectively) (LPF). Though depicted as separate devices, the individual mixer devices may be collectively referred to as a mixer, and the individual filter devices may be referred to as a filter. Indeed, the individual devices may be consolidated into one or more single components configured to process multiple signals. The filters may be implemented in a variety of configurations, including configurations incorporating passive and/or active filter components. Filtering may be achieved using a passive RC network, for example. Additionally, or alternatively, active components such as a digital signal processor may be employed to provide filtering. Filtering may be performed based on frequency and/or phase of incoming signals. Indeed, in some embodiments, a digital signal processor is employed to perform linear phase processing, so as to allow for rejection of unwanted signal components. To achieve the desired signal isolation, the digital signal processor may be configured to subtract, for a given transducer output, any out-of-phase, steady-state components.

An exemplary mode of operation for the depicted output processing subsystem will now be described. Referring specifically to transducer 12a, the transducer may be stimulated by application of the 0° variant of the sinusoidal local oscillator signal. This, in turn, results in movement of the transducer. As discussed above, the movement of the transducer may depend on various factors other than the characteristics of the input drive signal. Portions of sample 14 may, for example, bond to the surface of the transducer. The resulting variation in mass (i.e., from an unloaded state) would cause a change in the resonant frequency at which transducer 12a vibrates. In addition, various "acoustic" or "sonic" events can affect the movement of transducer 12a. For example, rupture events at or near the transducer surface (e.g., a portion of sample 14 breaking away from a bonding location on the transducer, or a breaking of chemical bonds within sample 14) may produce a pressure wave that acts upon the transducer.

The various different movements of transducer 12a contribute to the output signal arising on output line 18a. As discussed above, in most cases, it is preferable that the signal on output line 18a reflect only the physical characteristics of transducer 12a and/or events occurring within sample 14 in the immediate vicinity of transducer 12a. However, if transducers other than transducer 12a are simultaneously active, the signal on line 18a will typically include cross-transducer noise (i.e., noise resulting from the other active transducers).

For example, as discussed above, in many implementations, transducers 12a and 12b (as well as transducers 12c and 12d) are operatively coupled to a stationary base with a shared mechanical suspension. Assuming a non-ideal mechanical suspension, vibrations of transducer 12a may cause transducer 12b to vibrate, and/or vice versa, which in turn will contribute noise components to the electrical signals on lines 18a and/or 18b. Noise components can also arise from pressure waves propagating through a liquid sample, and from indirect electrical couplings in the transducer supporting circuitry, as also discussed above.

In many prior systems, these noise issues are avoided by activating only a single transducer at a time, or by ensuring that simultaneously active transducers are spaced apart so that noise contributions are attenuated. This may, however, limit the processing capacity of the sensor system. For example, constraints on the activation of transducers typically will limit the speed of the sensor system. In biological scanning applications, for example, use of such a sensor system may slow scanning operations and produce other processing bottlenecks.

When multiple transducers in the same area are simultaneously active, the depicted use of different phase-shifted variants of the base drive signal facilitates obtaining substantially noise-free output signals. Referring again to transducer 12a and its supporting circuitry, the signal on line 18a is applied to mixer section 36a, along with the same phase-shifted variant 30a (the 0° variant) that was applied as an input drive signal to transducer 12a. Use of the same variant that is used to drive the transducer may be referred to as a "synchronous" deployment within output processing subsystem 34, since the variant typically is in sync with the transducer output signal on line 18a. The mixing at section 36a creates sum frequencies and difference frequencies, which are selectively filtered using LPF 38a. LPF 38a is tuned to pass only a range of frequencies and phase corresponding to transducer 12a. The resulting signal on output line 40a is therefore substantially free of cross-transducer noise.

As indicated above, some cross-transducer noise coupling may occur. However, the predetermined phase differences between the transducer drive signals cause the noise from other transducers to have electrical characteristics that are distinct from the desired base output signal. The characteristics of the noise signal(s) allow the noise to be readily suppressed or removed via the frequency/phase dependent filtering that occurs at filters 38a, 38b, 38c and 38d. For example, assume transducers 12a and 12b are both activated at the same time with their respective phase-shifted oscillator variants (e.g., variants 30a and 30b). Movements of transducer 12a could produce a noise movement in transducer 12b, via pressure wave coupling occurring through the liquid in sample 14, or through the transducer mechanical suspension. This would contribute noise to the electrical output signal on line 18b. Additionally, or alternatively, a stray capacitance could couple noise onto the output line. However, the phase differences between the oscillator signals used with each transducer would cause such noise contributions to appear on line in a manner that would readily enable the noise to be filtered from the output signal.

More specifically, in certain multiple-transducer embodiments, employing different variants of a periodic signal may cause any "non-pure" (e.g., noisy) transducer output signal to have frequency components that are distinct from those of the noise-free base output. Without noise, for example, the signal on a given output line typically would have a frequency close or identical to that of the base local oscillator signal. Because different transducers within a given group would be driven with different phase-shifted versions of the local oscillator, their vibratory outputs would be staggered in time relative to one another. Accordingly, if vibration from more than one transducer were to contribute to the output on any given transducer output line, the resulting noisy output would have higher frequency components than the noise-free output. The noise components would then be filtered out by the combined operation of the mixer sections and frequency-/phase-based filtering.

As indicated above, use of different dive signal variants may be implemented in a number of different ways. The depicted illustrative embodiment may, for example, be extended to more or less than four drive signal variants that are equally distributed in phase over the period of the base oscillator signal. Assuming a modified system with N transducers, the modified system may be implemented with N corresponding drive signal variants, one for each transducer. The drive signal variants would be shifted in phase from the local oscillator by 0°, (1/N*360)°, (2/N*360)°, . . . and ((N−1)/N*360)°.

The drive signal circuitry that provides the signal variants to the transducers may also be implemented in many different ways. As shown in FIG. 1, each transducer group 12 may be provided with an oscillator subsystem 16 dedicated to that individual transducer group. Additionally, or alternatively, a global oscillator generator 96 (FIG. 2) may be provided to provide oscillator signals (and variants thereof) to the individual transducer groups 22, via multiplexing, switching and/or other devices/methods.

Figure 3:
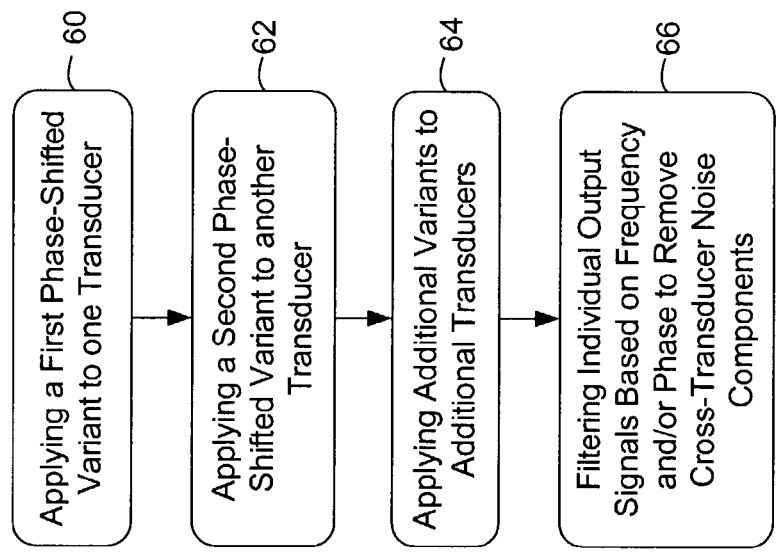
FIG. 3 depicts an exemplary implementation of a multiple-transducer sensing method according to the invention, in which multiple transducers may be employed at the same time.

A transducer-based sensor method will now be described with reference to FIG. 3. The method may be implemented in a variety of different ways. The following description is merely an illustrative example. As shown at 60 in FIG. 3, the exemplary implementation of the method includes applying a first phase-shifted variant of a periodic signal to a transducer. The implementation also includes applying a second, different variant of the periodic signal to another transducer, as shown at 62. As with the embodiments described above, further variants may be employed as desired and appropriate for a given application, as indicated at 64.

As explained above, the differences between the signal variants typically will cause signals associated with the two transducers to have different characteristics. This, in turn, will cause a noisy output signal (e.g., a signal having components associated with more than one of the transducers) to have characteristics that differ from those of the noise-free signal. Typically, the differences between a noisy signal and a noise-free signal manifest as differences in frequency or frequency ranges, such that noise suppression can be readily performed via bandpass filtering. Indeed, the depicted exemplary implementation includes, at 66, filtering output signals based on frequency to remove cross-transducer noise. Also, as explained above, phase discrimination methods may be employed in addition to or instead of frequency-based filtering.

It should be understood that the depicted implementation can be extended to more than two transducers and two corresponding drive signal variants. For example, as in the exemplary systems described above, it will often be desirable to employ four signal variants (e.g., respectively shifted in phase from a base signal by 0°, 90°, 180° and 270°) in a quadrature scheme with groups of four transducers. Indeed, it should be appreciated that the described method may be implemented in connection with the systems described above, and may thus be modified in accordance with the various different configurations that may be employed with those systems. It should be understood, however, that the method is broadly applicable and need not be implemented in connection with the particular systems described above.

It should be understood that the above systems and methods may be applied to a wide variety of multiple-transducer applications where it is desirable to obtain relatively noise-free outputs from individual transducers. As explained in the specific exemplary implementations discussed above, multiple variants of a drive signal are applied to different transducers in the system. Use of the different variations of the drive signal allow signal contributions from the different transducers to have different characteristics. This, in turn, facilitates suppression of noise components, through use of filtering or other techniques.

While the present embodiments have been particularly shown and described, those skilled in the art will understand that many variations may be made therein without departing from the spirit and scope defined in the following claims. The description of the invention should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A sensor system, comprising:
   a plurality of transducer groups, each containing a plurality of transducers in operative proximity with a sample material,
   where each transducer within each transducer group is actuated by receiving a different phase-shifted variant of a local oscillator signal, and
   where the phase-shifted variants of the local oscillator signal are selectively filtered during output processing to inhibit cross-transducer interference occurring between simultaneously active transducers.

2. The sensor system of claim 1, where the transducers within each transducer group are movably coupled to a base structure via a mechanical suspension.

3. The sensor system of claim 1, further comprising an oscillator subsystem configured to generate and apply the phase-shifted variants to the transducers within each transducer group, where within each transducer group, a variant shifted by 0° from the local oscillator signal is applied to a first transducer, a variant shifted by 90° from the local oscillator signal is applied to a second transducer, a variant shifted by 180° from the local oscillator signal is applied to a third transducer, and a variant shifted by 270° from the local oscillator signal is applied to a fourth transducer.

4. The sensor system of claim 3, where each transducer group includes only four transducers.

5. The sensor system of claim 1, where within each transducer group, each of the phase-shifted variants of the local oscillator signal is orthogonal to at least one other of the phase-shifted variants employed within such transducer group.

6. A sensor system, comprising:
   a plurality of transducer groups, each including a plurality of transducers for placement in operative proximity to a sample material, and an output processing subsystem configured to isolate output signals for each of the transducers within such transducer group by filtering out signal contributions caused by other simultaneously active transducers within such transducer group;
   where each transducer within each transducer group is actuated by receiving a different phase-shifted variant of a local oscillator signal, and
   where the sensor system is configured so that the phase-shifted variants of the local oscillator signal are selectively employed during output processing to inhibit cross-transducer interference occurring between simultaneously active transducers.

7. The sensor system of claim 6, where each output processing subsystem is configured to isolate output signals by employing a frequency-based filter.

8. The sensor system of claim 7, where the frequency-based filter is implemented at least partially with a digital signal processor.

9. The sensor system of claim 8, where the digital signal processor employs linear phase response processing to achieve unwanted signal rejection.

10. The sensor system of claim 6, where each output processing subsystem is configured to isolate output signals by employing a phase-based filter.

11. The sensor system of claim 10, where the phase-based filter is implemented at least partially with a digital signal processor.

12. The sensor system of claim 11, where the digital signal processor employs linear phase response processing to achieve unwanted signal rejection.

13. The sensor system of claim 6, where for each transducer within each transducer group, such transducer is driven by one of the phase-shifted variants, and the same phase-shifted variant is employed within an output signal path of such transducer to facilitate filtering out signal contributions caused by other simultaneously active transducers within such transducer group.

14. The sensor system of claim 13, where each transducer group includes four transducers that are driven by different phase-shifted variants that are respectively phase shifted from the local oscillator signal by 0°, 90°, 180° and 270°.

15. The sensor system of claim 13, where each transducer group includes N transducers that are driven by N corresponding phase-shifted variants that are respectively shifted in phase from the local oscillator signal by 0°, (1/N*360)°, (2/N*360)° . . . and ((N−1)/N*360)°.

16. The sensor system of claim 13, where the output processing subsystem includes a digital signal processor configured to filter the noise components in the output signal path.

17. The sensor system of claim 13, where each output processing subsystem includes a digital signal processor configured to process signal components using linear phase methods, and to subtract out-of-phase, steady-state components.

18. A transducer-based sensor method, comprising:
providing multiple different phase-shifted variants of a local oscillator signal to an array of transducers, where such providing includes:
applying a first one of the phase-shifted variants to a first transducer in the array; and
applying a second one of the phase-shifted variants to a second transducer in the array; and
filtering output signals from individual transducers in the array, where such littering is performed based on frequency to selectively remove signal components containing cross-transducer noise.

19. The method of claim 18, where providing multiple different phase-shifted variants of a local oscillator signal to an array of transducers further includes:
applying a third one of the phase-shifted variants to a third transducer in the array; and
applying a fourth one of the phase-shifted variants to a fourth transducer in the array.

20. The method of claim 19, where the first, second, third and fourth phase-shifted variants of the local oscillator signal each have a different phase relationship to the local oscillator signal.

21. The method of claim 20, where the first phase-shifted variant of the local oscillator signal is shifted in phase by 0° from the local oscillator signal, the second phase-shifted variant of the local oscillator signal is shifted in phase by 90° from the local oscillator signal, the third phase-shifted variant of the local oscillator signal is shifted in phase by 180° from the local oscillator signal, and the fourth phase-shifted variant of the local oscillator signal is shifted in phase by 270° from the local oscillator signal.

22. The method of claim 18, where the transducer array includes a plurality of transducer groups, each including a plurality of transducers, and where the providing and applying steps are performed at each of the transducer groups.

23. A transducer-based sensor method, comprising:
providing multiple different phase-shifted variants of a local oscillator signal to an array of transducers, where such providing includes:
applying a first one of the phase-shifted variants to a first transducer in the array; and
applying a second one of the phase-shifted variants to a second transducer in the array; and
filtering outputs of the transducers based on frequency to remove cross-transducer noise components and thereby obtain separate noise-free output signals corresponding to the first and second transducers.

24. A transducer-based sensor method, comprising:
providing multiple different phase-shifted variants of a local oscillator signal to an array of transducers, where such providing includes:
applying a first one of the phase-shifted variants to a first transducer in the array; and
applying a second one of the phase-shifted variants to a second transducer in the array;
filtering output signals from individual transducers in the array, where such filtering is performed based on at least one of frequency and phase to remove signal components containing cross-transducer noise; and
using the phase-shifted variants of the local oscillator signal to process output signals produced by the first and second transducers.

25. The method of claim 24, where using the phase-shifted variants of the local oscillator signal to process output signals produced by the first and second transducers includes:
using the first phase-shifted variant to process output from the first transducer; and
using the second phase-shifted variant to process output from the second transducer.

26. The method of claim 18, where providing multiple different phase-shifted variants of a local oscillator signal to an array of transducers is performed so that each of the phase-shifted variants is orthogonal to at least one of the other phase-shifted variants.

27. A transducer-based sensor system, comprising:
a transducer array including a plurality of transducers for placement in operative proximity to a sample material;
an oscillator network operatively coupled with the transducer array and configured to apply phase-shifted variants of a local oscillator signal to the plurality of transducers, where at least some of the plurality of transducers are actuated with different phase-shifted variants of the local oscillator signal; and
an output processing subsystem configured to filter output signals received from individual transducers in the transducer array, where the output processing subsystem is configured to perform such filtering based on frequency to remove cross-transducer noise components from such output signals.

28. The sensor system of claim 27, further comprising a base structure and a mechanical suspension movably coupling the plurality of transducers to the base structure.

29. The sensor system of claim 27, where the oscillator network is configured to generate and apply the phase-shifted variants to the transducers, and where the oscillator network is configured to apply a variant shifted by 0° from the local oscillator signal to a first transducer, a variant shifted by 90° from the local oscillator signal to a second transducer, a variant shifted by 180° from the local oscillator signal to a third transducer, and a variant shifted by 270° from the local oscillator signal to a fourth transducer.

30. The sensor system of claim 29, where the transducer array includes a plurality of transducer groups, each including four transducers, and where the oscillator network is configured to respectively apply a 0° variant, 90° variant, 180° variant and 270° variant to the four transducers within each transducer group.

31. The sensor system of claim 27, where each of the phase-shifted variants of the local oscillator signal is orthogonal to at least one other of the phase-shifted variants.

32. The sensor system of claim 27, where the output processing subsystem includes a digital signal processor configured to perform frequency-based filtering on the output signals.

33. The sensor system of claim 27, where the output processing subsystem includes a digital signal processor configured to process signal components using linear phase methods, and to subtract out-of-phase, stead-state components.

34. The sensor system of claim 27, where the transducer array includes a plurality of groups, each including a plurality of transducers.

35. A transducer-based sensor system, comprising:
a transducer array including a plurality of transducers for placement in operative proximity to a sample material;
an oscillator network operatively coupled with the transducer array and configured to apply phase-shifted variants of a local oscillator signal to the plurality of transducers, where at least some of the plurality of transducers are actuated with different phase-shifted variants of the local oscillator signal; and
an output processing subsystem configured to filter output signals received from individual transducers in the transducer array, where the output processing subsystem is configured to perform such filtering based on frequency to remove cross-transducer noise components from such output signals;
where the transducer array includes a plurality of groups, each including a plurality of transducers; and
where for each transducer within each transducer group, such transducer is driven by one of the phase-shifted variants, and the same phase-shifted variant is employed within an output signal path of such transducer to facilitate filtering out signal contributions caused by other simultaneously active transducers within such transducer group.

36. The sensor system of claim 35, where each transducer group includes four transducers that are driven by different phase-shifted variants that are respectively phase shifted from the local oscillator signal by 0°, 90°, 180° and 270°.

37. The sensor system of claim 34, where each transducer group includes N transducers that are driven by N corresponding phase-shifted variants that are respectively shifted in phase from the local oscillator signal by 0°, $(1/N*360)°$, $(2/N*360)°$ . . . and $((N-1)N*360)°$.

38. A transducer-based sensor system, comprising:
means for providing multiple different phase-shifted variants of a local oscillator signal to an array of transducers, where such means includes:
means for applying a first one of the phase-shifted variants to a first transducer in the array; and
means for applying a second one of the phase-shifted variants to a second transducer in the array; and
means for filtering output signals from individual transducers in the array, where such filtering is performed based on at least one of frequency and phase to remove signal components containing cross-transducer noise.

39. A sensor system, comprising:
a plurality of transducer groups, each including a plurality of transducers for placement in operative proximity with a sample material, and an output processing subsystem configured to isolate output signals for each of the transducers within such transducer group by filtering out signal contributions caused by other simultaneously active transducers within such transducer group based on phase-shifted variations between the signal contributions.

* * * * *

UNITED STATES PATENT AND TRADEMARK OFFICE
CERTIFICATE OF CORRECTION

PATENT NO. : 7,135,806 B2  
APPLICATION NO. : 10/286071  
DATED : November 14, 2006  
INVENTOR(S) : Daniel Robert Blakley Page 1 of 1

It is certified that error appears in the above-identified patent and that said Letters Patent is hereby corrected as shown below:

In column 9, line 22, in Claim 18, delete "littering" and insert -- filtering --, therefor.

In column 12, line 5, in Claim 37, delete "$((N-1)N*360)°$" and insert -- $((N-1)/N*360)°$ --, therefor.

Signed and Sealed this

Twenty-eighth Day of April, 2009

JOHN DOLL  
*Acting Director of the United States Patent and Trademark Office*